US006862936B2

(12) United States Patent
Kenderian et al.

(10) Patent No.: US 6,862,936 B2
(45) Date of Patent: Mar. 8, 2005

(54) LASER-AIR, HYBRID, ULTRASONIC TESTING OF RAILROAD WHEELS

(75) Inventors: Shant Kenderian, Baltimore, MD (US); B. Boro Djordjevic, Severna Park, MD (US); Donatella Cerniglia, Palermo (IT)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/637,125

(22) Filed: Aug. 8, 2003

(65) Prior Publication Data

US 2004/0056496 A1 Mar. 25, 2004

Related U.S. Application Data

(60) Provisional application No. 60/429,981, filed on Nov. 27, 2002.

(51) Int. Cl.$^7$ ................................................ G01N 29/04
(52) U.S. Cl. ........................................................ 73/636
(58) Field of Search ........................... 73/632, 633, 634, 73/636, 629, 146; 356/376; 702/184

(56) References Cited

U.S. PATENT DOCUMENTS

| | | | | |
|---|---|---|---|---|
| 3,558,876 A | * | 1/1971 | Tillman et al. | 246/169 S |
| 4,004,455 A | | 1/1977 | McKee | 73/67.9 |
| 4,174,636 A | | 11/1979 | Pagano | 73/636 |
| 4,235,112 A | | 11/1980 | Kaiser | 73/634 |
| 4,593,569 A | | 6/1986 | Joy | 75/636 |
| 5,419,196 A | | 5/1995 | Havria | 73/636 |
| 5,505,090 A | | 4/1996 | Webster | 73/657 |
| 5,574,224 A | | 11/1996 | Jaeggi | 73/636 |
| 5,636,026 A | | 6/1997 | Mian et al. | 356/376 |
| 5,698,787 A | | 12/1997 | Parzuchowski et al. | 73/643 |
| 5,801,312 A | | 9/1998 | Lorraine et al. | 73/602 |
| 5,824,908 A | | 10/1998 | Schindel et al. | 73/632 |
| 5,970,438 A | | 10/1999 | Clark et al. | 702/184 |
| 6,041,020 A | | 3/2000 | Caron | 367/149 |
| 6,055,862 A | | 5/2000 | Martens | 73/632 |
| 6,324,912 B1 | | 12/2001 | Wooh | 73/629 |
| 6,335,943 B1 | | 1/2002 | Lorraine et al. | 372/28 |
| 6,378,387 B1 | | 4/2002 | Froom | 73/865.8 |

OTHER PUBLICATIONS

Kenderian, Djordjevic and Green, "Laser–Based and Air Coupled Ultrasound as Noncontact and Remote Techniques for Testing Railroad Tracks," *Materials Evaluation*, vol. 60(1), Jan. 2002, pp. 65–70.

Kenderian, Djordjevic and Green, "Point and Line Source Laser Generation of Ultrasound for Inspection of Internal and Surface Flaws in Rail and Structural Materials," *Research in Nondestructive Evaluation*, vol. 13(4), Dec. 2001, pp. 189–200.

(List continued on next page.)

*Primary Examiner*—William Oen
(74) *Attorney, Agent, or Firm*—Larry J. Guffey

(57) ABSTRACT

A remote, non-contact system for detecting a defect in a railroad wheel as the wheel is stationary or moving along a railroad track includes; (1) a pulsed, laser light source for generating an ultrasonic wave in the wheel, the ultrasonic wave having a direct portion and reflected and transmitted portions if the direct portion encounters a defect in the wheel, (2) an optical component in the path of the light from the light source for forming the light into a specified illumination pattern so that the generated ultrasonic wave has a specified wavefront, (3) an air-coupled transducer or a group of transducers for sensing the acoustic signal emanating from the wheel that results from the ultrasonic wave traveling through the wheel, and (4) a signal processor, responsive to the sensed acoustic signal, capable of distinguishing whether the sensed signal has a component that indicates the existence of a reflected portion in the ultrasonic wave, wherein the presence of such a component in the acoustic signal indicates the existence of a defect in the railroad wheel.

17 Claims, 14 Drawing Sheets

OTHER PUBLICATIONS

Kenderian and Djordjevic, "Narrowband Laser–Generated Surface Acoustic Waves Using A Formed Source In The Ablative Regime," *Journal of Acoustical Society of America*, to be published, Spring 2003, no month.

Di Scalea, Kenderian & Green, Non–Contact Ultrasonic Inspection of Railroad Tracks, 45th International SAMPE Symposium, San Diego, CA, May 21–25, 2000.

Kenderian, Djordjevic and Green, Laser–Air Hybrid Ultrasonic Technique for the Inspection of Verical Cracks in Rails, 11th Inter. Symp. Nondestr. Char. Mater.—Berlin, Germany, Jun. 24–28, 2002.

Cerniglia, Kenderian, Djordjevic, Garcia & Morgan, "Laser and Air–Coupled Transducer For Non–contact Ultrasonic Inspection in the Railroad Industry," AIPnD Conf., Spring 2003, no month.

Kautz, "noncontact Determination of Antisymmetric Plarte Wave Velocity in Ceramic Matrix Composite," *Res. Nondestr. Eval.*, (1997) pp. 137–146, no month.

Baldwin, Berndt & Ehrlich, "narrowband Laser Generaation/Air–Coupled Detection: UltrasonicSystem For On–line Process Control of Composites," "Ultrasconics," 37, pp. 329–334 (1999), no month.

* cited by examiner

ULTRASONIC SIGNAL GENERATING MECHANISMS

PULSED LASER SOURCE    TEMPORAL AND/OR SPATIAL SHAPING OF THE PULSE (a)

Front View (b)

Side View

LASER-AIR, HYBRID, ULTRASONIC TESTING OF RAILROAD WHEELS

CROSS-REFERENCE TO RELATED APPLICATION

This application claims the benefit of U.S. Provisional Patent Application No. 60/429,981, filed Nov. 27, 2002 by Shant Kenderian, B. Boro Djordjevic and Donatella Cerniglia.

BACKGROUND OF THE INVENTION

1. Field of the Invention

This invention relates to non-contact remote ultrasonic testing of railroad wheels. More particularly, this invention relates to a method for using a Laser-Air Hybrid Ultrasonic Technique (LAHUT) as a noncontact and remote ultrasonic system for testing railroad wheels.

2. Description of the Related Art

Railroad maintenance is one of the greatest problems facing the transportation industry today. In one four-month period in 1998, a major railroad company experienced ten derailments due to broken rail at an expense of over $1.3 million. In its *Newsletter*, in Sep. of 2000, the Texas Research Institute estimated that every ninety minutes a derailment, an accident, or any other rail related incident takes place in the U.S.

For decades, optical methods (i.e., laser generation and interferometric detection of ultrasound) have been widely popular as noncontact and remote detection techniques for identifying flaws in structural materials. However, their efficiency relies heavily on the amount of light reflected back from the surface. As a result, the curvature, roughness and cleanliness of the reflecting surface all have a negative influence on the amount of light reflecting back to the optical detector. This, unfortunately, renders these techniques ineffective for many industrial applications, including the railroad industry.

Other than by visual inspection, no technique is readily available today to the railroad industry to perform inspections on railroad wheels while they are still mounted on a train. Prior acoustic inspection techniques have proved to be unreliable.

For example, an attempt was made to automate the inspection of rail wheels of passing trains (See: M. N. Fahmy, R. E. Finch, "Cepstrum analysis of surface waves in acoustic signature inspection of railroad wheels", J. Acoust. Soc. Am., Vol. 75 (4), April 1984, pp. 1283–1290) by striking the wheels with a set of hammers. As a result of the hammers' impact on the wheel, an acoustic wave was generated in the wheel and detected with air-coupled transducers. However, both the generating technique and the detecting transducer operated with low frequency sound, such that the signal was often indistinguishable from mechanical noise.

Today, wheels are inspected only when railroad cars are sent for maintenance in service shops. Only about 10% of the wheels are possibly inspected for flaws in service shops annually. There are approximately ten million rail wheels in service in the U.S.

The present inventors' early experiments utilizing non-contact, ultrasonic techniques for the inspection of railroad tracks and railroad wheels were initially disclosed in May 2000. See "Non-Contact Ultrasonic Inspection of Railroad Tracks," 45th International SAMPE Symposium, San Diego, Calif., May 21–25, 2000. The teachings and disclosure of this work is hereby incorporated by reference. The experimental techniques of this early work used laser beams focused to a point. These early techniques will be seen to differ significantly from those revealed herein. The present inventors have also documented much of their work on the inspection of railroad tracks and wheels in the scientific literature. See "Laser-Air Hybrid Ultrasonic Technique for Railroad Wheel Testing," *Materials Evaluation*, vol. 61(4) April 2003 pp. 505–511; "Laser-Based and Air Coupled Ultrasound as Noncontact and Remote Techniques for Testing Railroad Tracks," *Materials Evaluation*, vol. 60(1), January 2002, pp. 65–70; "Point and Line Source Laser Generation of Ultrasound for Inspection of Internal and Surface Flaws in Rail and Structural Materials," *Research in Nondestructive Evaluation*, vol. 13(4), December 2001, pp. 189–200, "Narrowband Laser-Generated Surface Acoustic Waves Using A Formed Source In The Ablative Regime," *Journal of Acoustical Society of America*, vol. 113(1), January 2003, pp. 261–266, "Laser-Based and Air Coupled Ultrasound as Noncontact and Remote Techniques for Testing Railroad Tracks," (Translated to Italian), *The Journal of the Italian Society of Nondestructive Testing Monitoring Diagnostics*, vol. 23(2), 2002, pp. 34–41, "Laser And Air-Coupled Transducer For Non-Contact Ultrasonic Inspection In The Railroad Industry (in Italian)," ENEA Trisaia Research Center (MT) Italy, "Il Giornale delle prove nondistructive monitoraggia," diagnostica, 1, 2003, pp. 27–32, "Laser-Air Hybrid Ultrasonic Technique for the Inspection of Rail Steel," *Nondestructive Characterization of Materials*, Berlin, Germany. Jun. 24–28, 2002, pp. 27–31, and "Sensitivity of Point And Line Source Laser Generated Acoustic Wave To Surface Flaws," *IEEE Transactions on Ultrasonics Ferroelectrics and Frequency Control*, To Be Published 2003. The teachings and disclosure of these works are hereby incorporated by reference.

In view of the lack of viable techniques for inspecting rail wheels in the field and the significant losses that occur in railway accidents attributable to wheel defect problems, it is seen that a great need exits for a testing method that can inspect rail wheels in the field.

3. Objects and Advantages

There has been summarized above, rather broadly, the prior art that is related to the present invention in order that the context of the present invention may be better understood and appreciated. In this regard, it is instructive to also consider the objects and advantages of the present invention.

It is an object of the present invention to provide a testing method for inspecting railroad wheels in the field.

It is another object of the present invention to provide a testing method that can test the railroad wheels of a stationary or moving train car.

It is yet another object of the present invention to provide a railroad wheel testing apparatus that can be maintained clear of the rail track and any obstacles along the test path.

It is a further object of the present invention to provide an ultrasonic railroad wheel testing method and apparatus that operates without establishing any contact with the surface of a rail wheel.

It is a still further object of the present invention to provide a rail wheel testing method and apparatus that provides superior signal-to-noise ratio (SNR) to that achieved with other non-contact ultrasonic methods, such as Electro-Magnetic Acoustic Transducers (EMATs) or measurements obtained with optical detection techniques of stress waves.

It is an object of the present invention to provide a rail wheel testing apparatus and method that allows for complete rail wheel inspection, on a moving or stationary rail car, including hard-to-reach areas such as the back surface (field-side) of the wheel.

It is another object of the present invention to provide an ultrasonic railroad wheel testing apparatus and method that detects both surface breaking and internal anomalies.

It is yet another object of the present invention to provide a rail wheel testing apparatus and method whose test signals can be processed via advanced signal analysis methods (e.g., frequency, feature extraction, wavelet and signal classifier methods) so as to enable automated signal recognition at rates not possible by manual means.

These and other objects and advantages of the present invention will become readily apparent as the invention is better understood by reference to the accompanying summary, drawings and the detailed description that follows.

SUMMARY OF THE INVENTION

Recognizing the need for the development of improved methods for detecting flaws in moving or stationary railroad wheels, the present invention is generally directed to satisfying the needs set forth above and overcoming the disadvantages identified with prior art devices and methods.

In accordance with the present invention, a preferred embodiment of it takes the form of a remote, non-contact system for detecting a defect in a railroad wheel as the wheel is stationary or moving along a railroad track. Such a system includes: (1) a pulsed, laser light source, located at a first specified location in the environment surrounding the wheel, for an generating ultrasonic wave in the wheel body, the ultrasonic wave having a direct portion and reflected and transmitted portions if the direct portion encounters a defect in the wheel, (2) optical components (lenses and mirrors) in the path of the light from the light source for focusing and forming the light into a specified illumination pattern so that the generated ultrasonic wave has a specified wavefront, (3) an air-coupled transducer, located at a second specified location in the environment, for sensing the acoustic signal emanating from the wheel that corresponds to the generated ultrasonic wave, and (4) a signal processor, responsive to the sensed acoustic signal, for distinguishing in the sensed signal the arrival times at the transducer of the various portions of the wave so that these differences and the known locations of the laser light source and transducer can be used to assist in distinguishing any reflected portion of the wave, wherein the presence of such a reflected portion in the acoustic signal indicates the existence of a defect in the surface of the railroad wheel.

Another preferred embodiment of the present invention takes the form of a remote, non-contact method for detecting a defect in a railroad wheel as the wheel is stationary or moving along a railroad track. Such a method includes the steps of: (1) generating in the railroad wheel an ultrasonic wave having a specified, controlled wavefront and frequencies, and (2) sensing the acoustic signal in the environment surrounding the wheel that corresponds to the generated ultrasonic wave and any of its secondary portions that are created when the wave encounters a defect on the surface of the wheel, wherein the presence of such secondary portions in the acoustic signal indicates the existence of a defect in the railroad wheel.

Thus, there has been summarized above, rather broadly, the present invention in order that the detailed description that follows may be better understood and appreciated. There are, of course, additional features of the invention that will be described hereinafter and which form the subject matter of the claims to this invention.

DESCRIPTION OF THE PREFERRED EMBODIMENT

Figure 1:
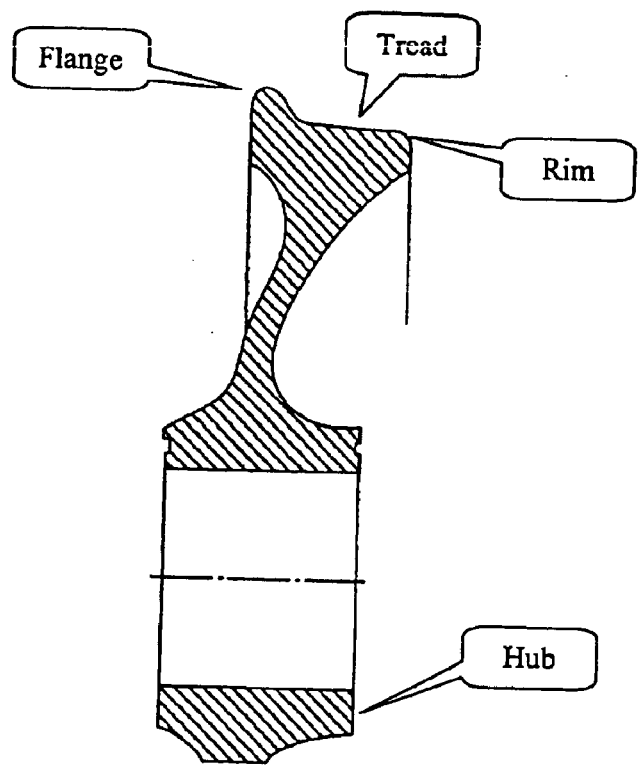
FIG. 1 illustrates the various sections of a rail wheel.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As previously mentioned, non-contact remote ultrasonic inspections are performed primarily by optical inspection methods. However, the efficiency of these methods depends heavily on the amount of light reflected back from the surface. As a result, the curvature, roughness and cleanliness of the reflecting surface all have a negative influence on the amount of light reflecting back to the optical detector. This, unfortunately, renders these techniques ineffective for many industrial applications including the railroad industry. A comparative study by the inventors between air-coupled and interferometric detection or EMF detection of ultrasound has demonstrated the superiority of the LAHUT over a purely Laser Based Ultrasonic (LBU) technique, within the operating frequencies of the air-coupled detector, i.e., below about 2.25 MHz.

Several types of defects are commonly seen to exist in railroad wheels. These may be classified according to their location in the wheel. For example, railroad wheel defects may be classified as to whether the defect occurs in the wheel's flange, tread, rim or side. See FIG. 1 for the definitions of the various sections of a rail wheel.

The ability to detect these defects may be affected by many factors, including: (1) rail wheel surface conditions, (2) rail wheel geometry, (3) the orientation and geometry of the defect, (4) electrical and/or mechanical noise introduced into the transducers being used, and (5) inadequate transducer-to-rail surface coupling. Some of these defects are especially worrisome as they can be very difficult to detected using the current state-of-the-art inspection method.

In an effort to remedy this situation and improve railway safety, the Center for Nondestructive Evaluation (CNDE) at the Johns Hopkins University undertook a major research effort to identify and develop new and improved rail wheel inspection technologies. This CNDE research has resulted in the invention of a Laser-Air Hybrid Ultrasonic (LAHU) approach with Formed Laser Sources (FLS) for the non-contact, remote testing of railroad wheels.

Figure 2:
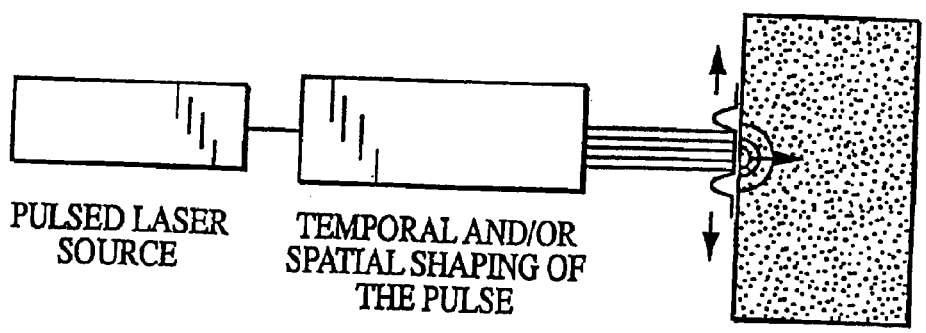
FIG. 2 illustrates FLS laser generation of controlled frequency and wavefront ultrasonic stress waves in a structural material.

Using this hybrid technique, multimode and controlled frequency and wavefront surface acoustic waves, guided waves, and bulk waves are generated to propagate on and within the rail wheels. See FIG. 2. The non-contact, remote nature of this methodology enables high-speed, full access inspections of rail wheels. By analog amplification, gating, digital signal capture, signal processing and digital data analysis and processing, such rail testing can be performed totally automated.

In a preferred embodiment, the present invention takes the form of a LAHU inspection apparatus that is fixed on the ground or mountable near a rail wheel. The present invention uses air-coupled transducer arrays that capture the acoustical signals from different locations for analysis. As the car moves along the rail, its wheels are tested for defects such as cracks. Data is collected with a data capture and storage unit, whereupon the data is processed and decisions are made with regards the integrity of the rail wheel.

The prior art of the present inventors includes teachings for the inspection of railroad tracks using laser beams focused to a point. This differs from the techniques of the present invention which disclose how control over the frequency content of the laser-generated acoustic wave and the shape of the wave front is obtained by projecting the laser beam to form specified geometrical arrangements or illumination patterns.

Figure 3:
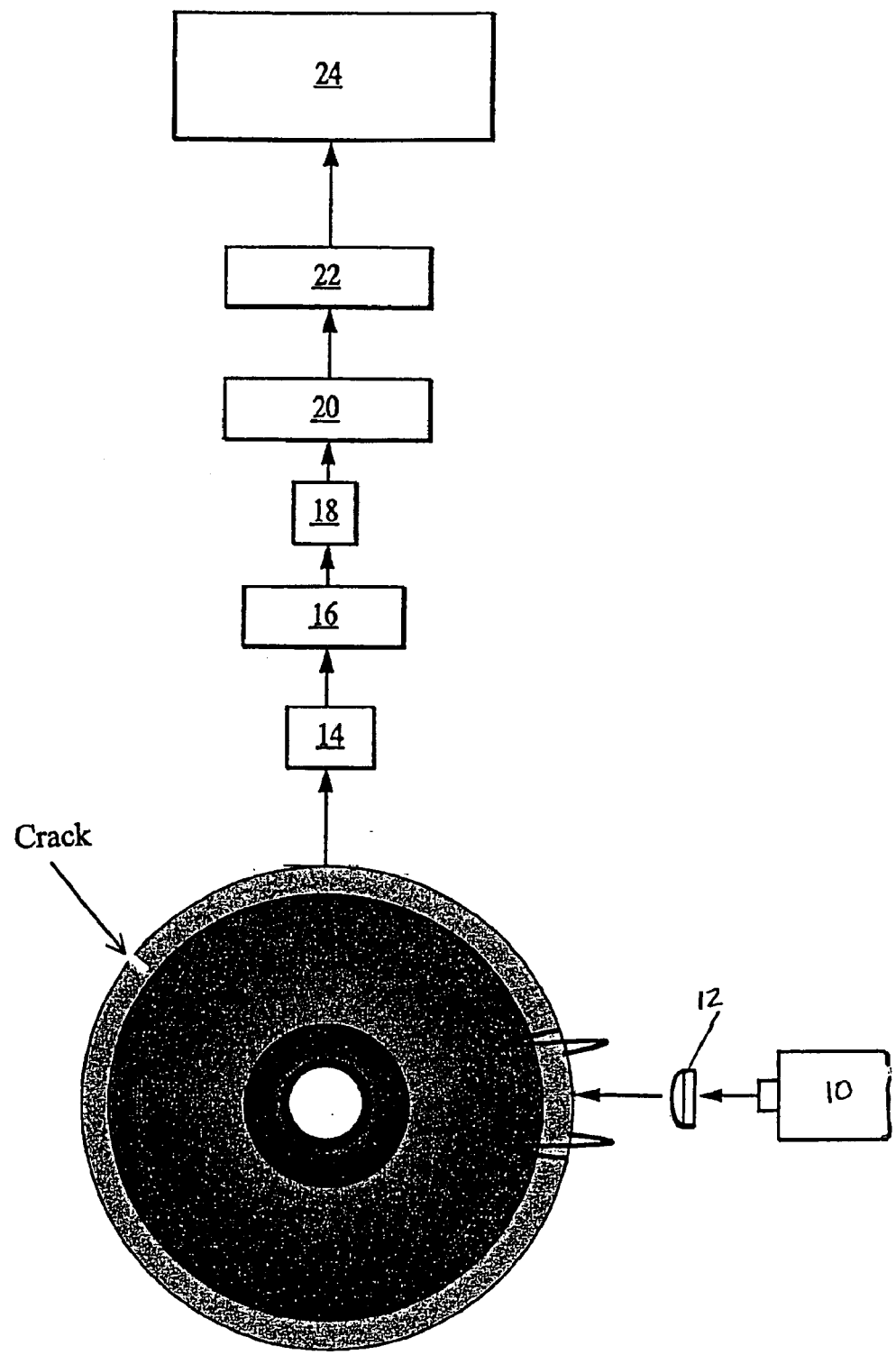
FIG. 3 illustrates schematically the arrangement of the elements of a preferred embodiment of the present invention for forming and controlling ultrasonic tests.

FIG. 3 illustrates schematically the arrangement of the elements of a preferred embodiment of the present invention for forming and controlling ultrasonic tests. It includes the following essential components: a light source 10 formed by mirror, lens and/or fiber optic assemblies 12, air-coupled sensors/transducers 14 that may be used in a direct path orientation or combined with acoustical mirrors and waveguides in a single or array arrangements, signal processing 16 means, including signal analog amplification, signal gating, signal digital conversion 18, data receiving 20, data storing 22, signal analysis 24, processing, and record storing components.

A detailed description of the various aspects of a preferred embodiment for the remote, non-contact defect or flaw detection system 1 of the present invention follows:

Generation of Ultrasound

A short FLS pulse laser 10 (e.g., pulsed laser, Nd:YAG 1.06 $\mu$m, with 1–10 nanosecond pulse having maximum energy in the range of 100–10,000 mJ per pulse) is used to generate controlled frequency and wavefront ultrasound, including bulk, surface, plate and other guided mode acoustic waves. The laser light can be delivered to a rail wheel through mirrors, fiber optic bundles, light pipes or combinations of optical components 12.

The laser light can operate in the thermoelastic, near-ablative, ablative or constrained acoustical source regimes. The constrained regime is attained by coating or wetting the surface of the rail with a layer of constraining compounds that are transparent to the laser wavelength. This includes water, oil, grease, graphite, glass, or transparent tape among a large number of other possible constraining layers. Operating the laser light in the ablative regime proves desirable because it provides strong ultrasonic signals which are easily detected with a capacitive air-coupled transducer.

To enhance the signal sensitivity to a specific type of crack, a controlled frequency and directed wavefront ultrasonic signals are generated using formed laser pulses. Formed laser light pulses are created by spatially modifying the shape, repetition and spacing of a light illumination area on the rail or by temporal modulating the pulse for the desired frequency. For example, experiments performed on a section of a rail wheel showed that an acoustic signal generated with a laser line source was more effective than that generated by a laser point source for the detection of surface breaking cracks in the wheel.

Detection of Ultrasound

For remote detection of ultrasound, capacitive air-coupled ultrasonic receivers 14 or gas ultrasonic wave detectors capable of detecting frequencies between 50 kHz and 3 MHz can be used. They are seen to be capable of operating at liftoff distances exceeding 15 cm and to not be critically dependent on precise orientation or alignment. Naturally, higher frequency components attenuate severely in air. Therefore, as the standoff distance between the air-coupled transducer and the specimen is increased, the upper limit of the frequencies retained by the detector is lowered.

Overall signal strength as a function of standoff distance follows an exponential behavior. Good signal was readily available up to 40 mm and useful measurements were possible past 80 mm. The optimum detection angle for a Rayleigh wave propagating in steel was found to is 6.5 degrees, with angular variation of ±2 degrees still retaining good signal intensity. Assuming an acoustic velocity in air of 0.333 mm/$\mu$s, a Rayleigh wave velocity in steel of 2.9 mm/$\mu$s and a 90° propagation angle of the Rayleigh wave in steel, Snell's law calculations steel confirmed the experimental observation of the critical refraction angle of 6.5 degrees in air.

Air-coupled ultrasound signal detection can be performed via transducers that detect receive-signals by facing the surface of the rail wheel directly. Acoustical mirrors and waveguides can be used to help in redirecting the sound fields to a detector. Waveguides enable capture of the signal at different angles from multiple locations and allow the receiving transducers to be placed at more flexible locations. Arrays of waveguides enable capture of ultrasonic signals from different locations. Horns can also be used to help in collecting, redirecting and intensifying the acoustic signal.

The techniques of the present invention have been found to be applicable to many structural materials in their industrial field conditions. That is, although thin layers of dirt, oxides, grease, and other contaminants can slightly dampen the signal detected by the air-coupled transducer, they have a more significant affect on enhancing the laser generated signal. As a result, a stronger signal is detected with the presence of such contaminants.

Thus, the techniques of the present invention can tolerate surface roughness reasonably well (i.e., although, pitting, spalling and porosities open to the surface can attenuate a surface wave to a great extent). For the rail wheels investigated in the development of the present invention, surface waves were generated on various regions of a rail wheel and detected successfully without the need for modifying the surface through cleaning or polishing. Furthermore, all sensor signals disclosed herein represent single events, i.e., averaging techniques were not necessary as a way to improve the signal to noise ratio. Although, they can be used for some specific purposes.

Data Capture and Processing

The data capture and signal processing 16 elements of the present invention includes signal analog amplification, signal gating, signal capture by digital means with multi-channel capability at resolutions as needed to process the signals. Ultrasonic signals are gated and analyzed in the time and frequency domains, classified via wavelet analysis or other feature and classification algorithms. Additional signal processing means include a dedicated signal classifiers and appropriate software 24 that are used to automatically characterize or assist in the characterization of existing defects in the rail wheels or other structural materials.

Methodology

The methodology of the present invention can be seen by reviewing the results achieved by measurements made to detect flaws that were placed on the surface of a 36 inch diameter calibration rail wheel. The wheel's four manufactured flaws were marked with the letters A, B, C, and D. A, B, and C were slots made to the wheel flange, tread, and rim, respectively, and D was a hole drilled in the side of the wheel.

The wheel was divided into 360 degrees. The location of zero degrees was determined from the point where the acoustic signal was generated, i.e., the point at which the generation laser illuminated the surface of the wheel. The positions of the detector and the flaw were referred to in terms of their location, in degrees, along the wheel circumference with respect to the acoustic source. The detector position was designated with the letter $\theta$, while that of the flaw with $\phi$. See FIG. 4 for a schematic of this experimental setup.

(a) Detection of a Defect in the Wheel's Flange

Figure 4:
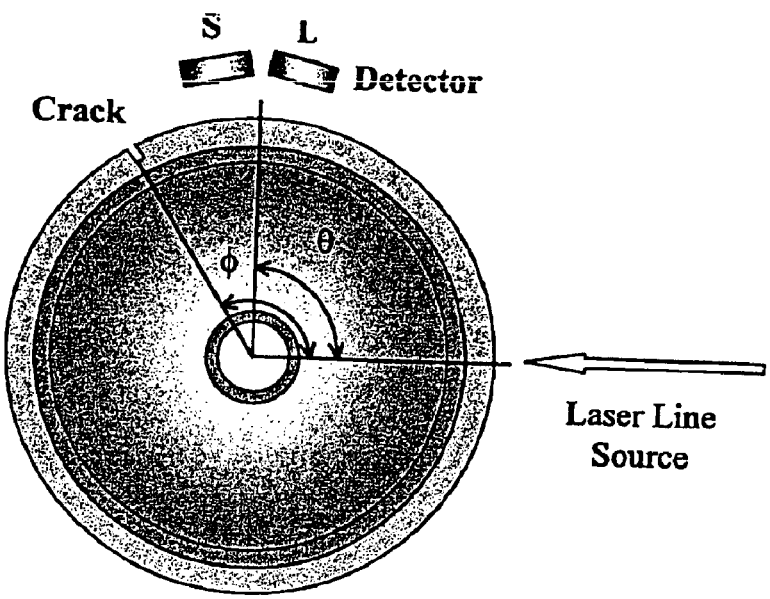
FIG. 4 illustrates schematically the arrangement of the experimental setup of the present invention.

In the detection of slot A, a 16 mm saw cut was made to the wheel flange to represent a surface breaking crack on the wheel flange. As shown in FIG. 4, the detector was kept at the $\theta=90°$ position. The wheel was rotated such that the slot fell in various positions between $\phi=-10°$ and 160°.

As noted previously, the optimum detection angle for a steel-to-air leaky Rayleigh wave is 6.5°. Therefore, a detector positioned between 0° and 180°, say 90°, and inclined at 6.5° from the surface normal, optimally detects a signal traveling the "Short Path", i.e., counterclockwise according to FIG. 4, traveling one quarter of the wheel circumference. Similarly, when this detector was inclined at 353.5° from the surface normal, it optimally detects a signal traveling the "Long Path", i.e., clockwise according to FIG. 4, traveling three quarters of the circumference. Short path and long path inclinations were denoted with the letters "S" and "L", respectively.

Figure 5:
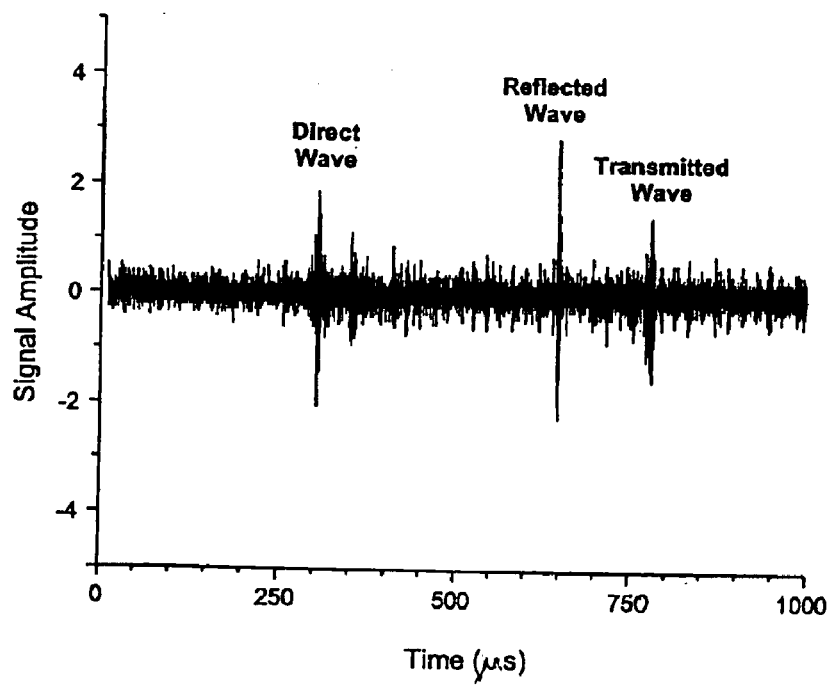
FIG. 5 shows a 1000 $\mu$sec portion of the acoustic signal detected with the present invention by a surface wave generated at 0° and detected at 90° when the observed defect or slot in the flange is located at $\phi$=150°.

A 17 mm long laser line source was used to generate the acoustic signal used for the detection of the 16 mm slot. Detector standoff distance was kept at 8 mm for long path detector inclination and 16 mm for short path inclination. FIG. 5 shows a broad view, 0–1000 $\mu$s, of a signal generated at 0° and detected at 90° with the detector in the long path L-inclination and slot A located at $\phi=150°$. Interestingly, the wheel geometry is such, that a Rayleigh wave completes one revolution around the wheel in approximately 1000 $\mu$s. This is obvious from the 3100 and 2928 mm circumference of the wheel flange and tread, respectively, and the 2.9797 mm/$\mu$s Rayleigh wave velocity in rail steel.

In FIG. 5, three main arrivals are observed. The first, at 285 $\mu$s, is a direct wave traveling 90° counterclockwise to the detector, propagating 775 mm in steel or one quarter the circumference of the flange, and 8 mm in air. Although the detector was not optimized for short path signal detection, or counterclockwise propagation in FIG. 4, a fraction of the strong direct signal was still detected. This was due to the large 10 mm aperture of the detector and small 8 mm standoff distance of the detector. Other factors also played an important role in the detection mechanism of the capacitive air-coupled transducer. Some of these factors include the direction of particle displacement of the acoustic signal in steel and air, attenuation through air and impedance between air and the detector membrane.

The second arrival, at 630 $\mu$s, is a reflected wave traveling from 0° past the detector at $\theta=90°$, counterclockwise, redirected upon reflection from slot A at $\phi=150°$, propagating back to the detector at $\theta=90°$, in a clockwise direction. The total propagation distance is 1808 mm in steel and 8 mm in air. The amplitude of the reflected wave is greater than that of the direct wave. The reason for this is that with its L-inclination, the detector was optimized for the detection of signals propagating in the clockwise rather than the counterclockwise direction, according to the setup shown in FIG. 4.

The third arrival, observed at 800 µs, is a transmitted wave traveling clockwise from 0° to slot A at φ=150°, transmitting through the slot and continuing in a clockwise direction to the detector at θ=90°. The total propagation distance is 2325 mm in steel, traveling three quarters of the circumference of the flange, and 8 mm in air.

Considering a Rayleigh wave velocity of 2.9797 mm/µs in rail steel and a wave velocity of 0.3333 mm/µs in air, the calculated arrival times of all three waves agree well with the observed signals. The amplitude of the transmitted wave was smaller than the direct and reflected waves mainly because of the substantially longer propagation path in steel, which would effectively increase signal attenuation.

While the acoustic source and receiver were stationary, the wheel was rotated so that slot A changed its position with respect to generation and detection points. The "Direct" and the "Transmitted" waves did not change their position in the time domain. This is because their propagation distances did not change with the wheel's rotation. However, the arrival time of the reflected wave varied with the rotation of the wheel for obvious reasons.

Figure 6:
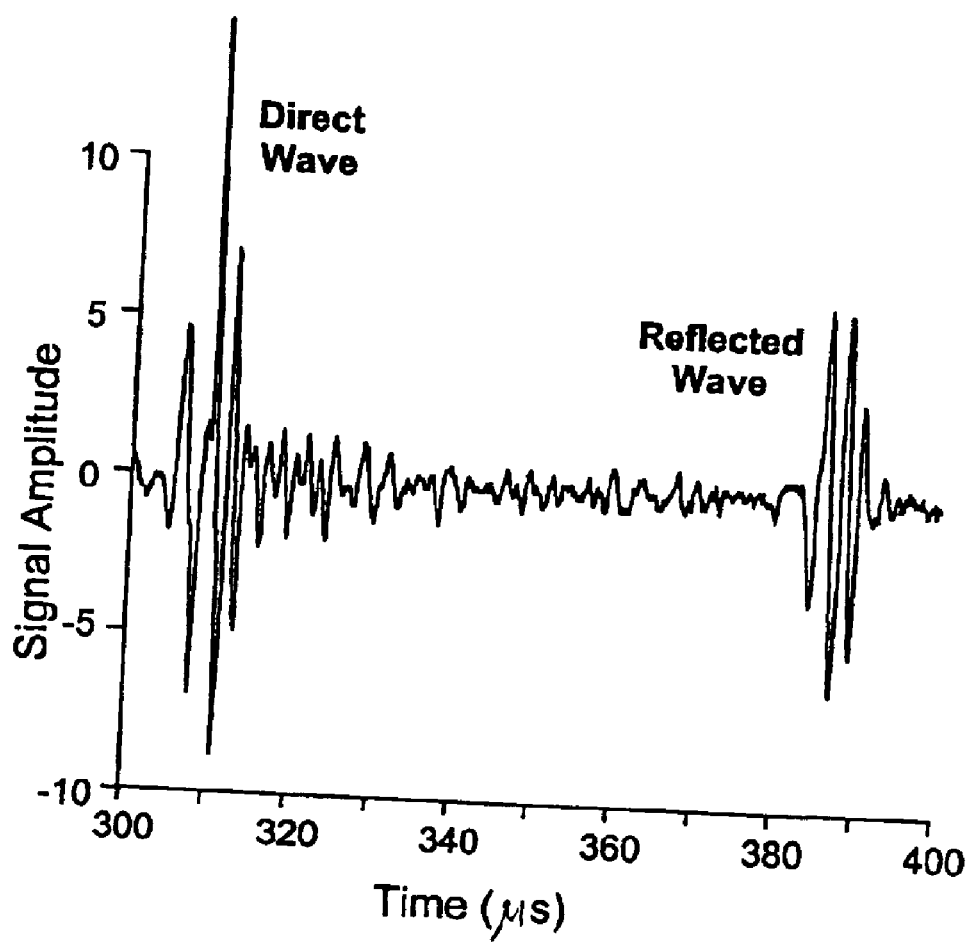
FIG. 6 shows a result for the experimental setup shown in FIG. 5 but with the slot positioned at $\phi$=−13°.

Using this technique, successful detection of slot A was possible for positions between 0° and 180°. Detection capacity was not limited to this range, except that, for positions between 180° and 360°, a better signal was obtained using a detector in the short path S-inclination to detect a reflected wave propagating in the counterclockwise direction. FIG. 6 shows results obtained with the detector in the S-inclination positioned at θ=90° and slot A positioned at φ=−13°.

Figure 7:
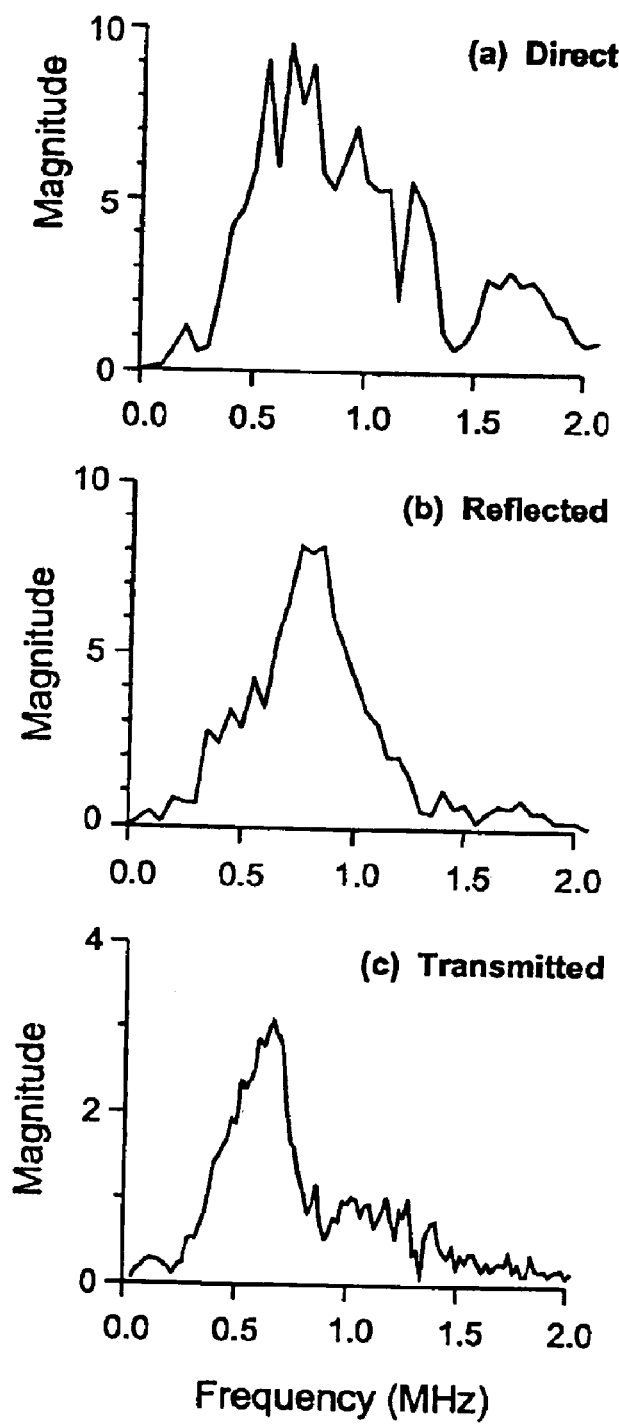
FIGS. 7a–7c show the frequency analysis of the direct, reflected and transmitted ultrasonic waves detected and shown in FIG. 5.

Frequency analysis of the direct, reflected and transmitted ultrasonic waves is presented in FIG. 7. FIG. 7a shows that the upper and lower boundaries of the frequency of the direct wave are set by the 0.3 MHz high pass filter used in this experiment and the 2.0 MHz detection limit of the capacitive air-couple transducer.

As a general rule, wavelengths smaller than the depth of a crack reflect back from the crack while those with larger wavelengths transmit through. At its deepest point, slot A is 5.25 mm deep. A Rayleigh wavelength of 5.25 mm corresponds with a frequency of 0.57 MHz in steel. Accordingly, frequencies higher than 0.57 MHz are expected to reflect back from slot A and those lower than 0.57 MHz to transmit through.

FIGS. 7b and 7c show the frequency spectrum of the reflected and transmitted waves, respectively. For the reflected wave, a sharp decline is observed at frequencies lower than 0.6 MHz, while the frequency of the transmitted wave is confined between 0.3 MHz and 0.75 MHz, as expected.

(b) Detection of a Defect in the Wheel's Tread

A similar test configuration was used in the detection of slot B, a 26 mm long saw cut made to represent a surface breaking crack on the center of the wheel tread. A 25 mm long laser line source was used to generate the acoustic signal for the detection of the 26 mm slot. Detector standoff distance was kept at 25 mm throughout this part of the experiment.

Figure 8:
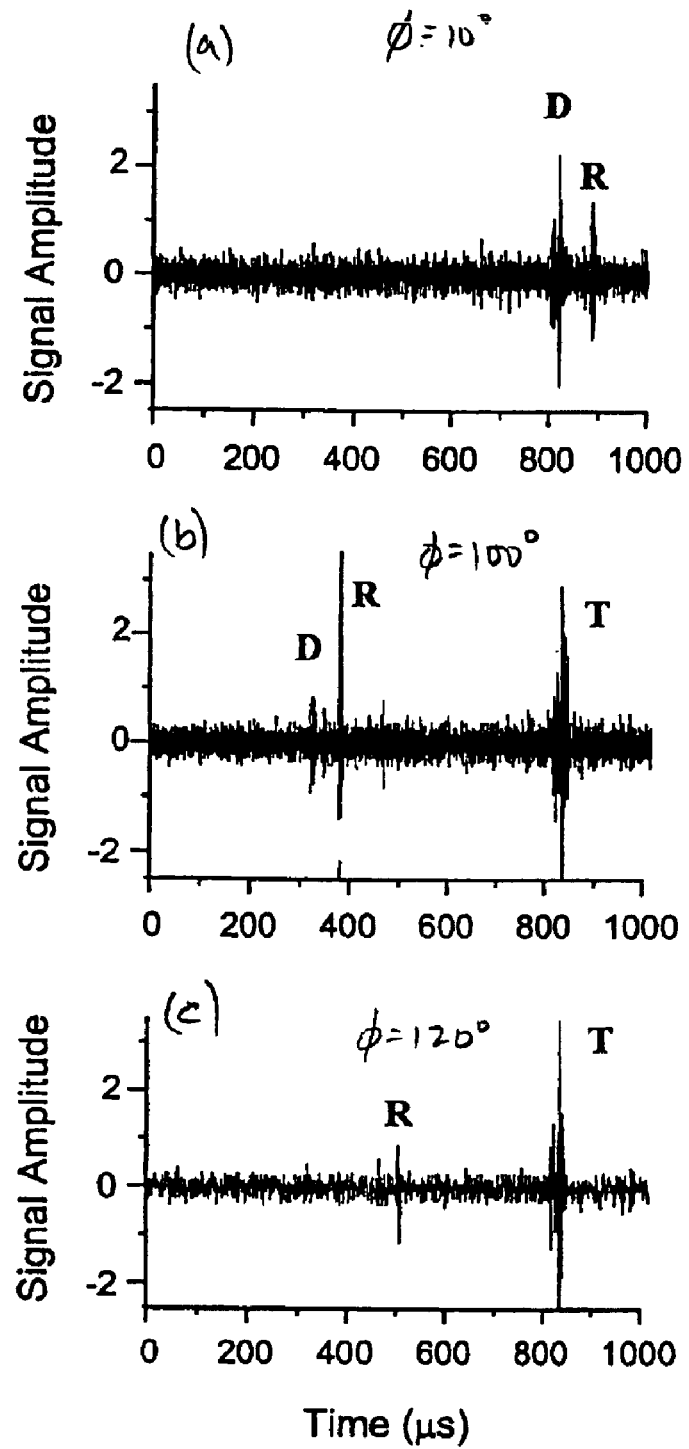
FIGS. 8a–8c show a 1000 $\mu$sec portion of the acoustic signal detected with the present invention by a surface wave generated at 0° and detected at 90° when the observed defect or slot in the wheel tread is located at $\phi$=10°, 100° and 120°, respectively.

FIG. 8 shows a broad view of a signal generated at 0° with the detector in the long path inclination positioned at θ=90° and slot B at φ=10°, 100° and 120°. Similar to the results previously shown in FIG. 5, three main arrivals are also observed in FIG. 8. The direct and transmitted waves travel one and three quarters of the circumference of the wheel tread, respectively. Therefore their arrival time can be predicted and was unchanged with the rotation of the wheel.

While these waves were stationary in the time domain, as shown in FIG. 8, the arrival time of the reflected wave would change with crack position φ. Because the transducer was oriented in the long path direction, it was not optimized for the detection of any waves approaching from the short path direction. Accordingly, the transmitted wave is absent in (a) and the direct wave is absent or weak in (b) and (c).

In FIG. 8a, the arrival time of the direct wave, approaching the detector from the long path direction, is 833 µs. The reflected wave from slot B at φ=10° propagates an additional distance of 163 mm to arrive 56 µs later. Similarly, when the slot is positioned at φ=100°, the reflected wave propagates an additional distance of 163 mm to arrive 56 µs behind the direct wave, as shown in FIG. 8b. In FIG. 8c, the corresponding delay associated with the reflected wave from a slot positioned at φ=120° is 168 µs so that the arrival time of the reflected wave would be 496 µs.

(c) Detection of a Defect on the Wheel's Rim

Figure 9:
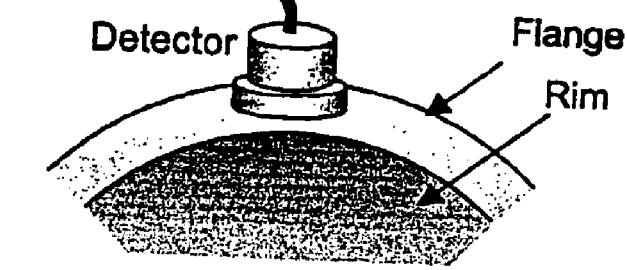
FIG. 9 shows a schematic drawing of the present invention's detector position with respect to the rim edge for use in those applications where a slot in the rim's edge is to be detected.
Figure 9:
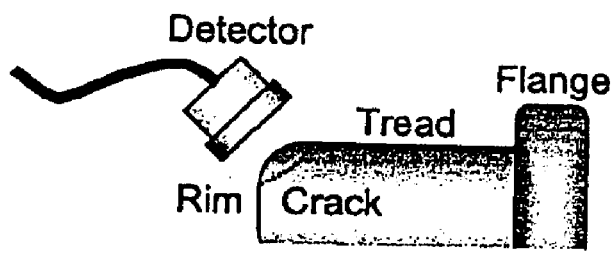

A similar procedure was followed for the detection of slot C, which was located at the rim edge of the wheel tread. A schematic drawing of the detector position with respect to the rim edge, shown in FIG. 9, demonstrates that, due to the roundness of the rim edge and curvature of the wheel tread, the area of the wheel surface available to the detector is limited to a large extent.

Should a contact transducer be used, this interface would be reduced to a point. However, due to the noncontact nature of the capacitive air-coupled transducer and its 10 mm aperture, the transducer was capable of detecting acoustic signals propagating along the rim edge of the wheel tread, although some limitations were imposed. That is, reflected and transmitted signals were not as distinct as those presented earlier for the wheel tread and flange. In spite of the fact that the wheel flange had a round edge similar to that of the rim, the acoustic signal was somewhat confined to the body of the flange and interacted more pronouncedly with slot A, which extended through most of the flange width.

In contrast, along the rim edge the acoustic signal was free to spread upward towards the tread and downward towards the hub. In addition, due to the geometry of the rim edge, slot C was deep in the center but was quickly reduced to a shallow crack along the edges. The length of slot C did not extend to a significant portion along the rim width the way slot A did along the flange. These factors, acting collectively, reduced the detectability of slot C in comparison to the detectability of slots A and B.

The air-coupled transducer was positioned at θ=90° in the short path inclination with standoff distance of 20 mm. By rotating the wheel, slot C fell inside and outside the detection range of the transducer. Positioning the transducer in the short path inclination, at θ=90° limited the detection range of slot C to positions φ between 0° and 90°.

Figure 10:
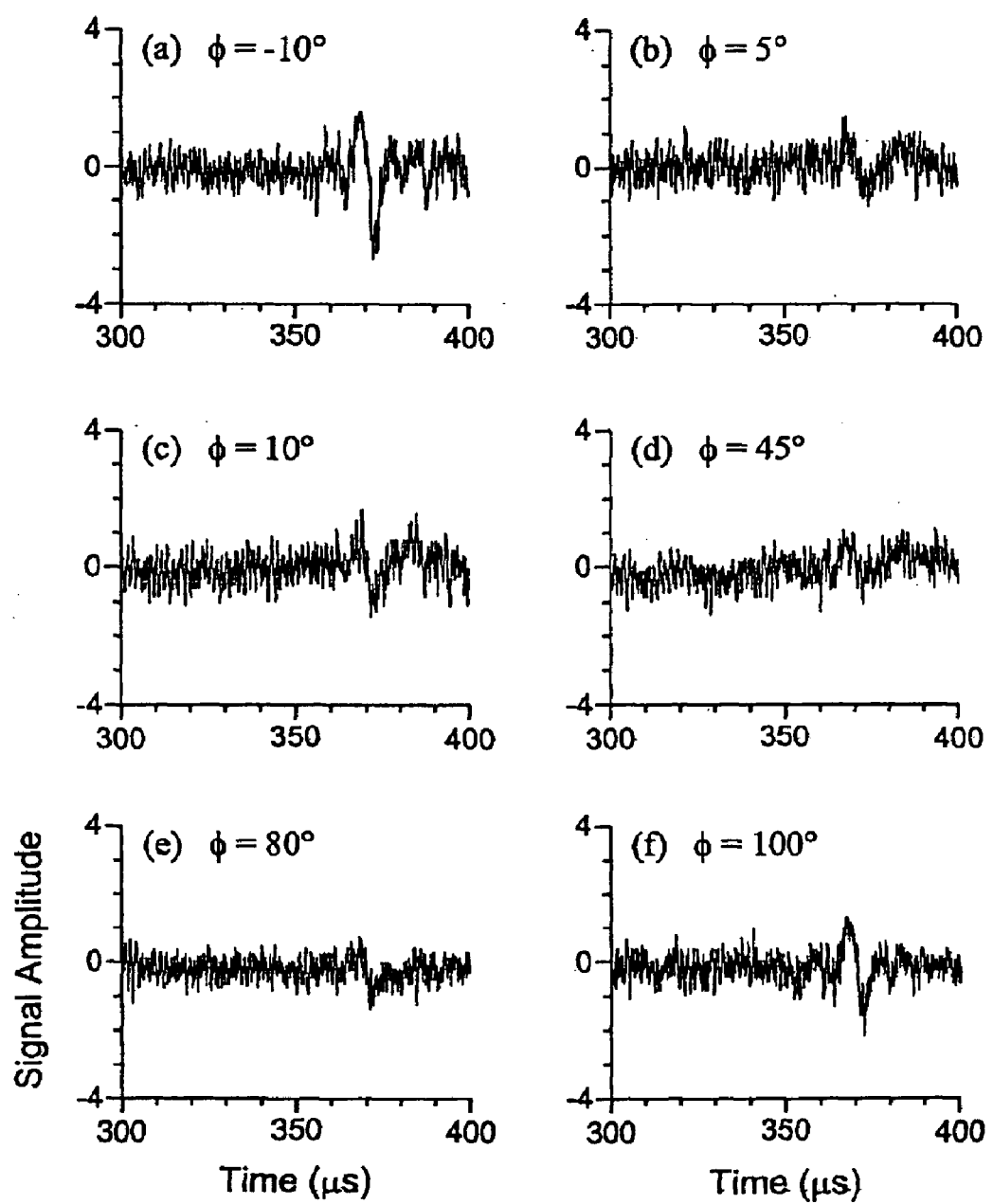
FIGS. 10a–10f show a 400 $\mu$sec portion of the acoustic signal detected with the present invention by a surface wave generated at 0° and detected at 90° when the observed defect or slot in the wheel's rim edge is located at $\phi$=−10°, 5°, 10°, 45°, 80° and 100°, respectively.

FIG. 10 shows a close-up of the direct signal propagating counterclockwise to the detector for a variety of slot positions φ. In FIGS. 10a and 10f, slot C fell outside the detection range of the transducer, therefore a viable direct signal was received by the detector. Inside the detection range, the direct signal attenuated upon transmission through the slot, as shown in FIGS. 10b through 10e. The results demonstrate that this Laser Air Hybrid Ultrasonic Technique is capable of detecting cracks along the rim edge of the wheel tread. However, the detected signals were not as pronounced as those obtained for the wheel flange and tread, as shown in FIGS. 5 and 8.

(d) Detection of a Defect on the Side of the Wheel's Flange

A 3.3 mm hole was drilled in the side of the flange and marked with the letter D. The hole was too small to produce a considerable effect on an acoustic signal transmitting through the hole. With the detector kept at $\theta=10°$ and standoff distance of 21 mm, the wheel was rotated so that the hole was sometimes positioned between generation and detection, i.e., at $0°<\phi<10°$, and sometimes outside this region, i.e., at $10°<\phi<10°$.

Figure 11:
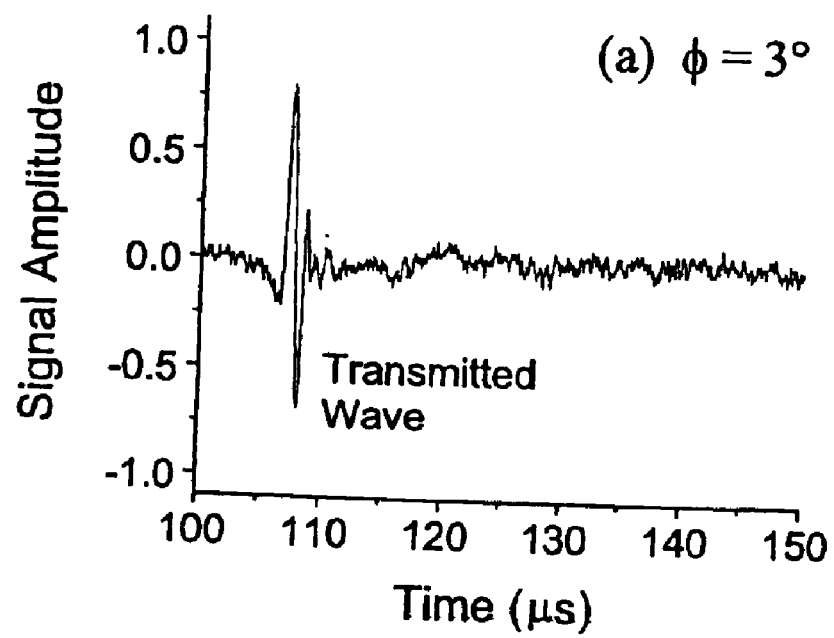
FIGS. 11a–11b show a 150 $\mu$sec portion of the acoustic signal detected with the present invention by a surface wave generated at 0° and detected at 10° when the observed defect or a hole in the side of the wheel's flange is located at $\phi$=3° and −3°, respectively.
Figure 11:
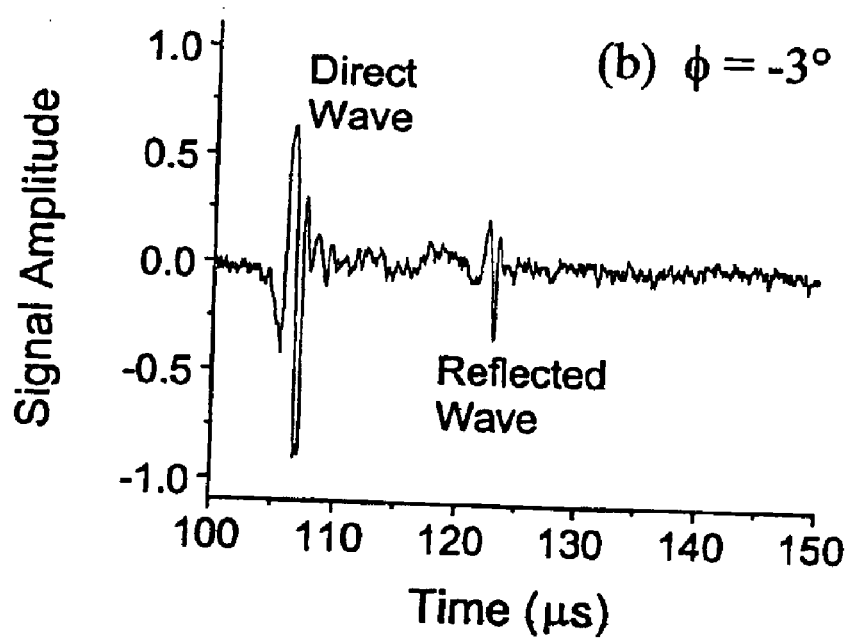

When the hole was inside this region, between generation and detection the amplitude of the transmitted signal, FIG. 11a, was not considerably different from that of the direct signal, FIG. 11b. However, FIG. 11b shows that when the hole was outside this region and with proper inclination of the air-coupled detector, a reflected component of the acoustic signal could be detected to make possible the detection of a small hole such as that represented by D.

Figure 12:
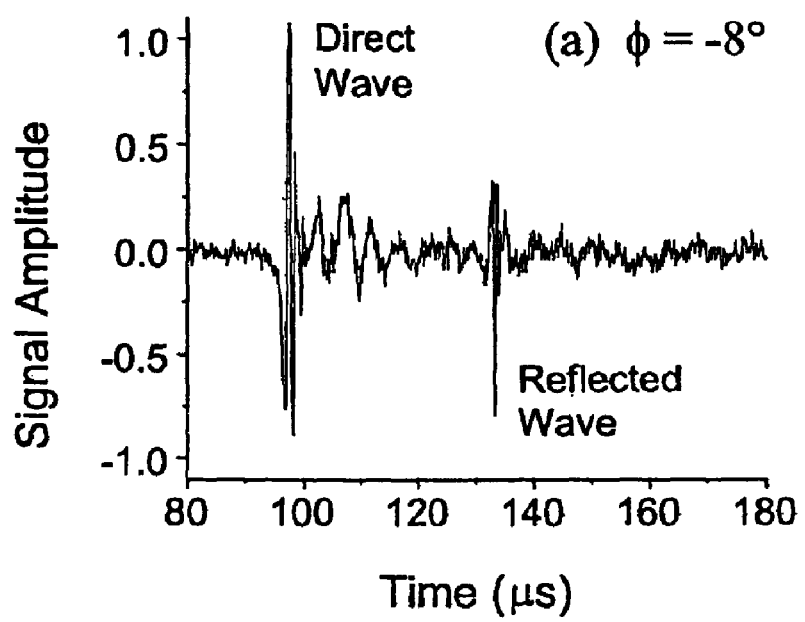
FIGS. 12a–12b show a 180 $\mu$sec portion of the acoustic signal detected with the present invention by a surface wave generated at 0° and detected at 10° when the observed defect or a hole in the side of the wheel's flange is located at $\phi$=−8° and −13°, respectively.
Figure 12:
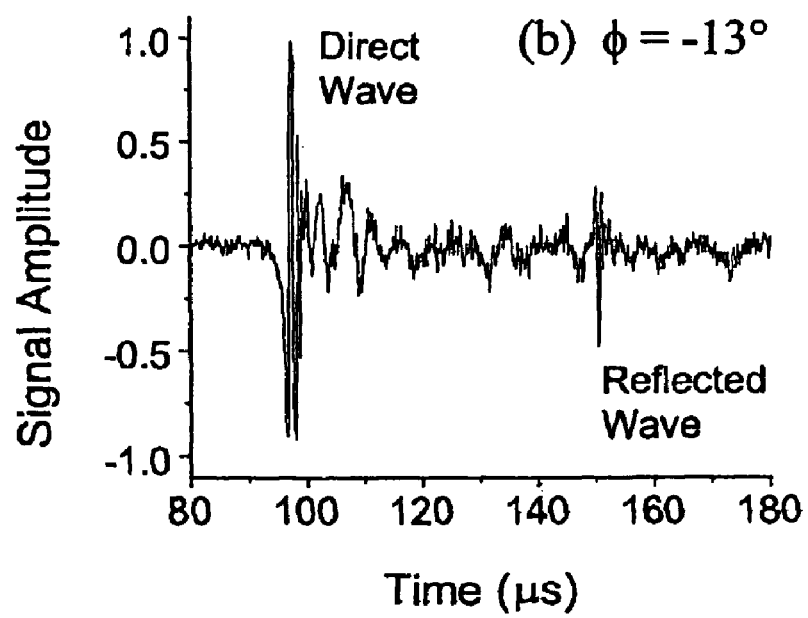

FIG. 12 shows similar results obtained with the hole positioned at $\phi=-8°$ and $-13°$. Due to the curvature of the wheel, a detector fixed at $\theta=10°$ was capable of detecting the hole as far as $\phi=-15°$. Beyond this range, the hole, generation source and detector fell out of alignment and the hole was no longer within detection range of the current experimental setup.

Application of Methodology to Various Measurement Schemes

The use of the present invention introduces a new degree of flexibility to rail wheel inspection operations and enables them to be performed with a test station that is located between and on the side of a rail track.

Figure 13:
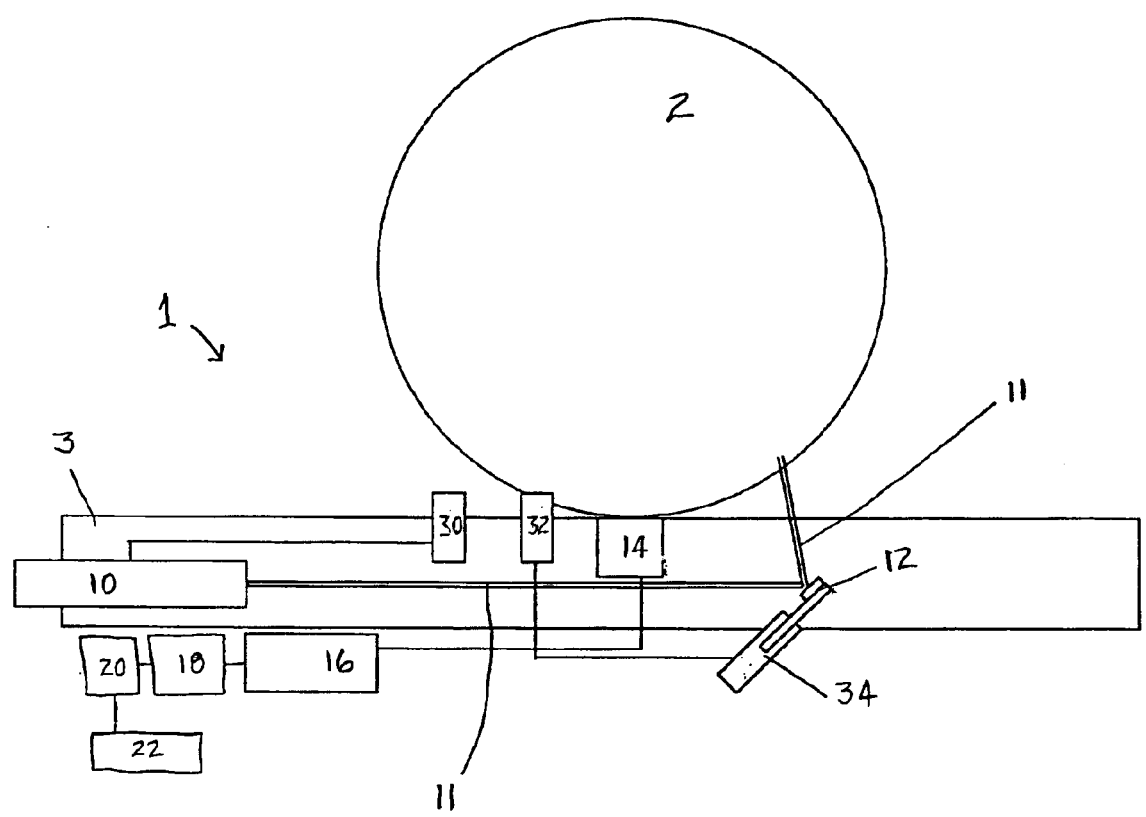
FIG. 13 illustrates schematically a preferred embodiment of the present invention in the form of test stand that is used to inspect a rail wheel that moves along a rail track.

FIG. 13 shows the basic components needed for such a test stand as it is used to inspect a rail wheel 2 sitting on a track 3. These components include a pulse laser 10 that issues a laser beam 11, a mirror and lens assembly 12, position sensors 30, 32 that sense the approach of a to-be-inspected rail wheel and trigger the laser 10 and activate linear and rotary motion components 34 that move the mirror and lens assembly 12 into its desired location and orientation with respect to the oncoming wheel, an air-coupled detector 14 and signal processing 16, signal digital conversion 18, data receiving 20, data storing 22, signal analysis 24, processing, and record storing components.

As the wheels roll by the test station, position sensors trigger the FLS system such that the wheel testing occurs with the wheel and sensors in their desired positions. The FLS generates selected acoustic signals in a wheel, signature ultrasonic signals are received by the air coupled detectors and collected via digital data capture and storage unit. The signals are automatically processed via signal feature extraction software, classified and decisions are made regarding the integrity of the rail wheel. The data can be stored locally or transmitted by any means to remote control center for additional processing analysis or any other management actions.

Various schemes have been trialed for orienting the components of the present invention in relation to the track and an oncoming rail wheel. These are briefly discussed below.

(a) Scheme 1

Figure 14:
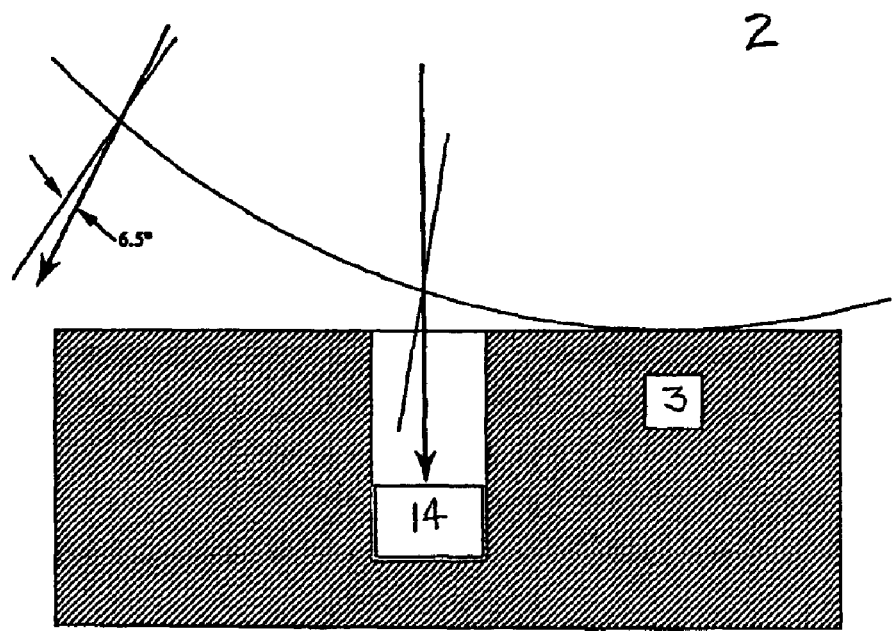
FIG. 14 illustrates schematically a scheme for orienting the detector of the present invention so that it is embedded in the rail track on which the to-be-inspected wheel is to move.

A Rayleigh wave propagating along the surface of steel transmits to the air at 6.5° from the normal to the surface. This may be taken into consideration in the design of the test configuration. The laser pulse may be timed such that the Rayleigh wave transmitted at 6.5° from the surface of the wheel propagates at 0° with respect to the normal to the surface of the rail track. A detector may then be embedded in the rail track such that the signal propagating through the air arrives at the detector through an appropriate opening in the rail track, as shown in FIG. 14. Alternatively, the wheel may be raised slightly, being supported on the flange instead of the tread, in order to protect the detecting transducers from damage.

(b) Scheme 2

Figure 15:
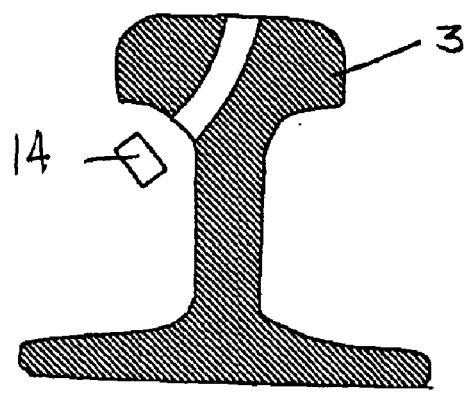
FIG. 15 illustrates schematically a scheme for orienting the detector of the present invention so that it is in a protective housing that faces an opening made in the rail track to guide the acoustic signal to the detector.

To protect the sensitive surface of the detector from water, dust, or debris falling from the opening made to the rail track, as was shown in the example in FIG. 14, the detector 14 may be placed in a protective housing, such that the sensitive surface of the detector is not facing the opening made to the rail track directly and is not subject to water, dust, or falling debris. Wave guides may be used to guide the acoustic signal through opening in the rail and to the detector, as shown in the example in FIG. 15.

(c) Scheme 3

Figure 16:
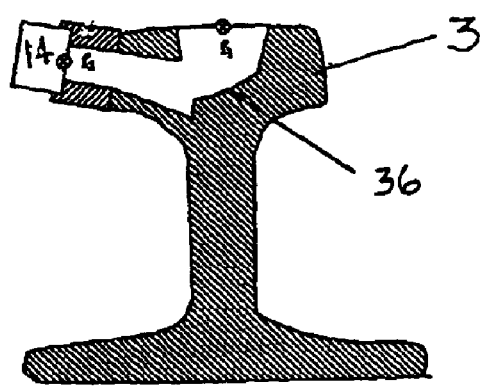
FIG. 16 illustrates schematically a scheme for orienting the detector of the present invention in a manner similar to that shown in FIG. 15 but where the opening in the rail track has been machined to focus the acoustic signal at the detector.

To increase the signal strength at the detection point, the acoustic signal may be received through the opening in the rail track and focused at the point of detection. An elliptical segment 36 may be machined in the rail track with one focal point of the ellipse at the center of the opening along the top surface of the track, and the other focal point at the center of the sensitive surface of the detector. The elliptical segment 36 is to be considered only in the region where the acoustic signal is expected to impact. The remaining regions, which are expected to receive only noise, should be coated with a sound absorbent material and/or made to reflect the sound wave away from the detector. See the example shown in FIG. 16.

(d) Scheme 4

Figure 17:
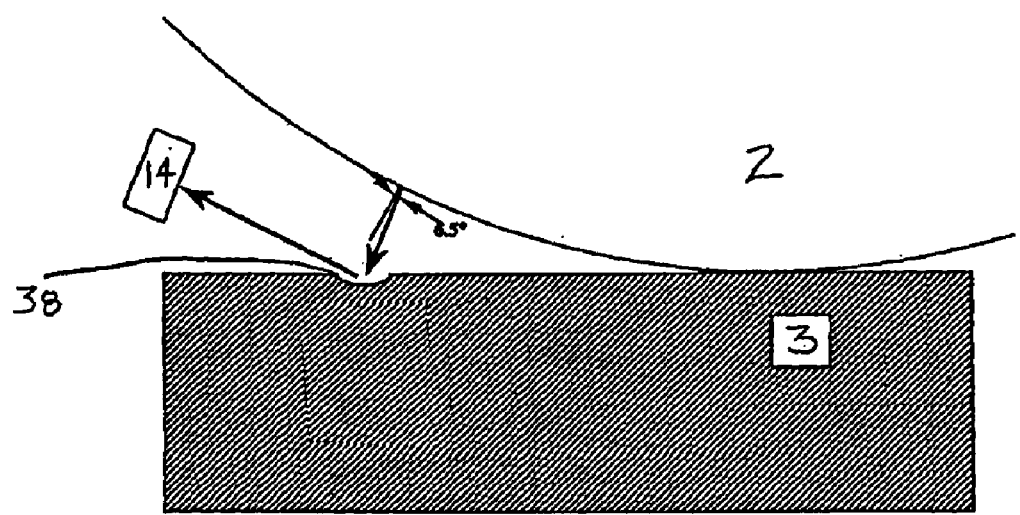
FIG. 17 illustrates schematically a scheme for orienting the detector of the present invention so that it is in a protective housing that faces an ultrasound mirror dimple made in the rail track so that the signal propagating along the surface of the rail wheel reflects from the dimple on the rail and arrives at the detector which is positioned safely outside the wheel path.

This scheme does not rely on an embedded detector or an acoustic wave approaching the rail track at 0° inclination from the normal to the surface. Instead, shallow ultrasound mirror dimples 38 are made in the rail track so that the signal propagating along the surface of the rail wheel, leaks to the air, reflects from the dimples on the rail, and arrives at the detector. The detector can then be positioned safely outside the wheel path. See the example shown in FIG. 17.

(e) Scheme 5

Figure 18:
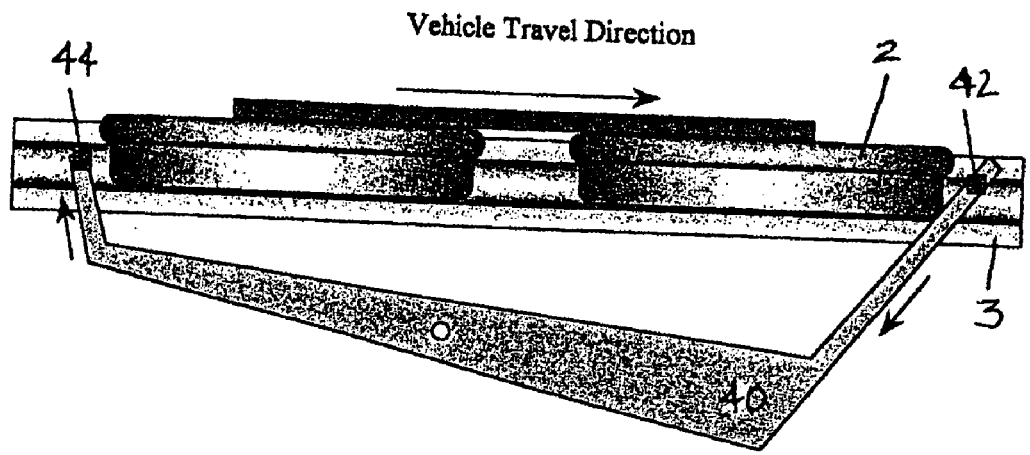
FIG. 18 illustrates schematically a scheme for orienting the detectors of the present invention on a lever that is actuated by the movement of the wheel to correctly position for a brief period the detectors in the path of the rail wheel.

A lever 40 may be designed and positioned in the path of the rail wheel 2. Upon contact between an angled arm on the lever and the wheel, the lever slides to position an array of detectors 42 in front of the front wheel and another array 44 behind the back wheel. Sensors are also positioned on the lever so that to trigger the laser when all detectors are in position. See the example shown in FIG. 18.

(f) Scheme 6

For point-to-point inspection of the wheel, a large number of generation and detection points are needed. With this scheme, these inspections can be performed with a single generation and detection point configuration. Position sensors, laser mirrors, lenses, and air-coupled or optical detectors can be configured on a platform mounted on a special track parallel to the rail track. The sensors on the platform sense the rail wheel and move the platform such that to maintain a relatively fixed position between the platform and the rail wheel for a distance exceeding one revolution of the wheel. While the platform maintains a fixed position with respect to the rail wheel, the laser is triggered at a repetition rate that would satisfy the coverage resolution needed to perform the inspection operation on the rail wheel.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention as set forth in the following claims for the present invention.

What is claimed is:

1. A remote, non-contact system for detecting a defect in a railroad wheel, said system comprising:
    a remote means, located at a first specified location in the environment surrounding said wheel, for generating in a non-contact manner in said wheel an ultrasonic wave having a specified wavefront, said ultrasonic wave having a direct portion and reflected and transmitted portions if said direct portion encounters a defect in said wheel,
    a non-contact means, located at a second specified location in said environment, for sensing from said wheel the acoustic signal emanating from said wheel that results from said ultrasonic wave traveling through said wheel,
    a signal processing means, responsive to said sensed acoustic signal, capable of distinguishing whether said sensed signal has a component that indicates the existence of a portion chosen from the group consisting of reflected and transmitted portions in said ultrasonic wave,
    wherein the presence of said component in said acoustic signal indicates the existence of a defect in said railroad wheel.

2. A defect detection system as recited in claim 1, wherein said specified wavefront is chosen so as to yield said wave having frequencies that match the frequency sensing capabilities of said non-contact, sensing means.

3. A defect detection system as recited in claim 1, wherein said ultrasonic wave generating means is modulated so as to yield said wave having frequencies that match the frequency sensing capabilities of said non-contact, sensing means.

4. A defect detection system as recited in claim 2, wherein said ultrasonic wave generating means is modulatable so as to yield said wave having frequencies that match the frequency sensing capabilities of said non-contact, sensing means.

5. A defect detection system as recited in claim 1, wherein said defect is of a specified type and said specified wavefront is chosen so as to enhance the sensitivity of said non-contact, sensing means to said specified type of defect.

6. A defect detection system as recited in claim 1, wherein when said defect is a surface defect, said specified wavefront is generated with a formed laser source.

7. A remote, non-contact method for detecting a defect in a railroad wheel, said method comprising the steps of:
    generating, in a non-contact manner in said railroad wheel an ultrasonic wave having a specified wavefront, said generated ultrasonic wave having a direct portion and reflected and transmitted portions if said direct portion encounters a defect in said wheel,
    sensing from said railroad wheel the acoustic signal in the environment surrounding said wheel that emanates from said wheel as a result of said ultrasonic wave traveling through said wheel,
    processing said sensed acoustic signal to determine whether said sensed signal has a component that indicates the existence of a portion chosen from the group consisting of reflected and transmitted portions in said ultrasonic wave,
    wherein the presence of said component in said acoustic signal indicates the existence of a defect in said railroad wheel.

8. A defect detection method as recited in claim 7, further comprising the step of choosing said specified wavefront so as to yield said ultrasonic wave having frequencies that match the frequency sensing capabilities encountered in said sensing step.

9. A defect detection method as recited in claim 7, further comprising the step of choosing the frequency of said ultrasonic wave so that said chosen frequency is compatible with the frequency sensing capabilities encountered in said sensing step.

10. A defect detection method as recited in claim 8, further comprising the step of choosing the frequency of said ultrasonic wave so that said chosen frequency is compatible with the frequency sensing capabilities encountered in said sensing step.

11. A defect detection method as recited in claim 7, wherein said defect is of a specified type and said specified wavefront is chosen so as to enhance the signal sensitivity encountered in said sensing step to said specified type of defect.

12. A remote, non-contact system for detecting a defect in a railroad wheel, said system comprising:
    a pulsed, laser light source, located at a first specified location in the environment surrounding said wheel, for generating in said wheel an ultrasonic wave, said ultrasonic wave having a direct portion and reflected and transmitted portions if said direct portion encounters a defect in said wheel,
    an optical component in the path of the light from said light source for forming said light into a specified illumination pattern so that said generated ultrasonic wave has a specified wavefront,
    an air-coupled transducer, located at a second specified location in said environment, for sensing from said wheel the acoustic signal emanating from said wheel that results from said ultrasonic wave traveling through said wheel,
    a signal processor, responsive to said sensed acoustic signal, capable of distinguishing whether said sensed signal has a component that indicates the existence of a reflected portion in said ultrasonic wave,
    wherein the presence of said component in said acoustic signal indicates the existence of a defect in said railroad wheel.

13. A defect detection system as recited in claim 12, wherein said specified wavefront is chosen so as to yield said wave having frequencies that match the frequency sensing capabilities of said transducer.

14. A defect detection system as recited in claim 12, wherein said pulsed laser is modulated so as to yield said wave having frequencies that match the frequency sensing capabilities of said transducer.

15. A defect detection system as recited in claim 13, wherein said pulsed laser is modulated so as to yield said wave having frequencies that match the frequency sensing capabilities of said transducer.

16. A defect detection system as recited in claim 12, wherein said defect is of a specified type and said specified wavefront is chosen so as to enhance the sensitivity of said transducer to said specified type of defect.

17. A defect detection system as recited in claim 12, wherein said defect is a surface defect in a railroad wheel, and said controlled wavefront is generated with a formed laser source.

* * * * *